United States Patent [19]

Becker et al.

[11] 4,232,887
[45] Nov. 11, 1980

[54] LACTONE COMPOUNDS CONTAINING AN INDOLIZINE RADICAL

[75] Inventors: William J. Becker; Sheldon Farber; Troy E. Hoover, all of Appleton, Wis.

[73] Assignee: Appleton Papers Inc., Appleton, Wis.

[21] Appl. No.: 17,764

[22] Filed: Mar. 5, 1979

[51] Int. Cl.³ .............................................. B01M 5/16
[52] U.S. Cl. .................... 282/27.5; 427/151; 544/115; 544/117; 544/127; 546/121; 544/345; 546/94; 546/116; 544/350; 546/89
[58] Field of Search ............... 282/27.5; 544/115, 117, 544/127, 345, 350; 546/89, 94, 116, 121; 427/151

[56] References Cited

U.S. PATENT DOCUMENTS

| | | | |
|---|---|---|---|
| 3,916,070 | 10/1975 | Ozutsumi et al. | 282/27.5 |
| 3,958,815 | 5/1976 | Poot et al. | 282/27.5 |
| 4,020,068 | 4/1977 | Farber | 282/27.5 |

Primary Examiner—Paul M. Coughlan, Jr.
Attorney, Agent, or Firm—E. Frank McKinney; Paul S. Phillips, Jr.

[57] ABSTRACT

Chromogenic compounds of normally colorless form are disclosed having the following structural formula:

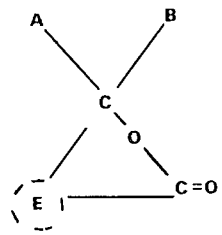

wherein E represents a six-membered aromatic or heterocyclic ring which may have an aromatic condensed ring and both the E ring and the condensed ring may be substituted, A represents an optionally substituted aminophenyl, indolyl, benzoindolyl, julolidinyl or kairolyl radical or the radical represented by B, and B represents a family of indolizine radicals. The compounds of this invention are eligible for use in pressure-sensitive and heat sensitive record materials and manifold marking systems.

83 Claims, No Drawings

LACTONE COMPOUNDS CONTAINING AN INDOLIZINE RADICAL

TECHNICAL FIELD

This invention pertains to novel chromogenic compounds which can give intense colors when they are contacted with an electron accepting co-reactant. More specifically, this invention relates to chromogenic compounds eligible for use in pressure-sensitive or heat-sensitive mark-forming record systems. Such systems are improved by use of these compounds. As used in mark-forming systems, marking in desired areas on support webs or sheets may be accomplished by effecting localized reactive contact between the chromogenic material and the electron accepting material on or in such a web or sheet, such material being brought thereto by transfer, or originally there in situ, the desired reactive contact forming colored images in the intended image-marking areas.

The chromogenic compounds of this invention have the following general formula:

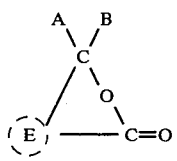

wherein E represents a benzene nucleus which is unsubstituted or substituted by one or more halogen, alkyl or dialkylamino groups, or, as a heterocyclic ring, E represents mainly a nitrogen containing heterocycle of aromatic character such as a pyridine or pyrazine ring. The ring E may also contain a condensed aromatic ring representing, for example, a naphthalene, quinoline or quinoxaline ring, which may be substituted by one or more halogen groups, A represents an optionally substituted aminophenyl, indolyl, benzoindolyl, julolidinyl or kairolyl radical, or the radical represented by B, B represents a family of indolizine radicals.

BACKGROUND ART

Several different types of chromogenic lactone compounds are described in U.S. Pat. No. 23,024, U.S. Pat. Nos. 3,491,112, 3,491,116, 3,509,173, 3,540,909, 3,540,911, 3,540,912, 3,736,337, 3,775,424, 3,853,869 and 4,020,068 and in Belgian Pat. No. 844,962.

U.S. Pat. No. 3,958,815 describes carbinol ether compounds containing indolizinyl groups.

DISCLOSURE OF THE INVENTION

Colorable novel chromogenic lactone compounds having indolizine radicals have been discovered. These compounds are initially substantially colorless but produce colored products on reaction with certain acid materials. It is an object of this invention to provide compounds containing such indolizine radicals, methods for making them and mark-forming record systems containing them.

It is another object of this invention to provide indolizine-containing compounds which produce substantially the same color of mark with different types of acid reactants.

It is yet another object to provide such compounds which produce colored marks which are resistant to actinic radiation.

The compounds of this invention produce substantially more color on one or more types of acid reactant surfaces than do the carbinol ether compounds disclosed in the prior art.

Important groups of colorable chromogenic lactone compounds having these indolizine radicals may be defined by the formula:

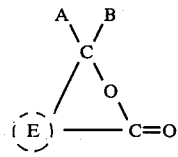

wherein E represents an optionally substituted benzene, pyridine, pyrazine, quinoline or quinoxaline ring, A represents an optionally substituted aminophenyl, indolyl, benzoindolyl, julolidinyl or kairolyl radical, and B represents a family of indolizine radicals hereinafter defined.

Among the more important compounds of this invention are the ones defined by the formula:

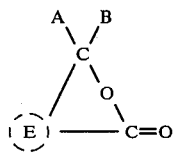

wherein E represents an optionally substituted benzene, pyridine, pyrazine, quinoline or quinoxaline ring, A represents an optionally substituted aminophenyl, indolyl, benzoindolyl, julolidinyl or kairolyl radical, and B represents an indolizine radical selected from:

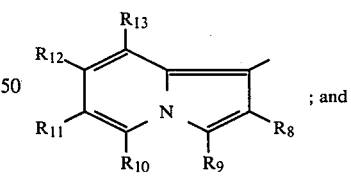

; and

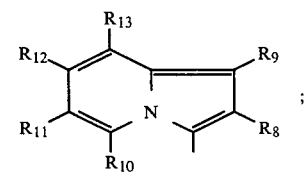

;

wherein $R_8$ represents aryl, substituted aryl, pyridyl, and alkyl; $R_9$ represents hydrogen, alkyl, aryl and benzyl; $R_{10}$, $R_{11}$, $R_{12}$ and $R_{13}$ represent hydrogen, alkyl, halogen and nitro.

The more preferred among the compounds of this invention are the ones represented by the following formulas:

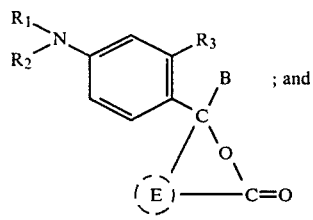

; and

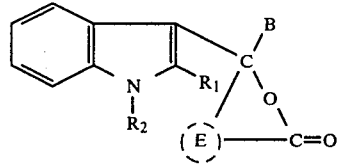

wherein E represents an optionally substituted benzene, pyridine, pyrazine, quinoline or quinoxaline ring, and B represents an indolizine radical selected from:

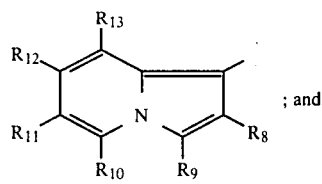

; and

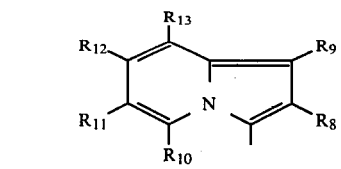

$R_1$ and $R_2$ represent hydrogen and alkyl, $R_3$ represents hydrogen and alkoxy, $R_8$ represents alkyl, pyridyl, aryl and substituted aryl, $R_9$ represents hydrogen, alkyl and aryl, $R_{10}$, $R_{11}$, $R_{12}$, and $R_{13}$ represent hydrogen, alkyl and nitro.

Most preferred among the compounds of this invention are those represented by the following formulas:

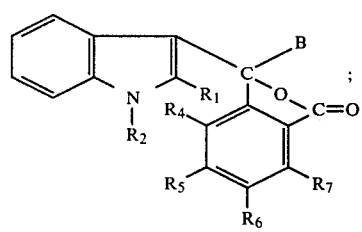

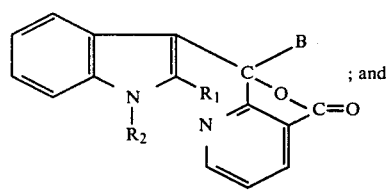

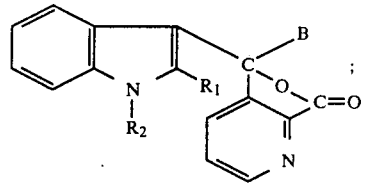

wherein B represents an indolizine radical selected from:

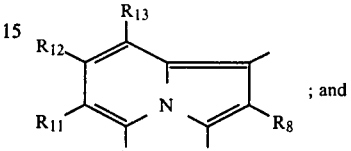

; and

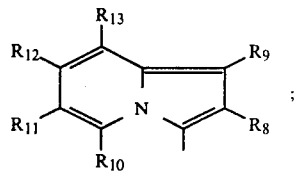

;

$R_1$ and $R_2$ represent hydrogen and alkyl, $R_4$, $R_5$, $R_6$ and $R_7$ represent hydrogen, chlorine and dialkylamino, $R_8$ represents aryl, substituted aryl, pyridyl and alkyl, $R_9$ represents hydrogen, alkyl, aryl and benzyl, $R_{10}$, $R_{11}$, $R_{12}$ and $R_{13}$ represent hydrogen, alkyl and nitro.

Advantageously, the lactone compounds according to this invention are manufactured by reacting a compound of the formula:

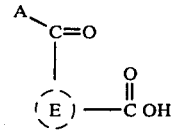

hereinafter called the keto acid, with an indolizine compound, hereinafter called substrate reactant B, wherein A, E, and B are as previously defined.

This reaction is desireably carried out by allowing the reactants to react together in the presence of an acidic dehydrating agent.

BEST MODE FOR CARRYING OUT THE INVENTION

The chromogenic compounds of this invention are eligible for use in pressure-sensitive and thermally-sensitive mark-forming systems. Pressure-sensitive mark-forming systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation preferably comprises microcapsules containing liquid solvent solution. The microencapsulation process utilized can be chosen from the many known in the art. Well known methods are disclosed in U.S. Pat. Nos. 2,800,457, 3,041,289, 3,533,958, 3,755,190, 4,001,140 and 4,100,103. Any of these and other methods are suitable for encapsulating the liquid solvent containing the chromogenic compounds of this invention.

The method of marking comprises providing a chromogenic compound of the present invention and bringing such chromogenic compound into reactive contact, in areas where marking is desired, with an acidic color-activating substance to produce a colored form of the chromogenic compound.

The acidic materials can be any compound within the definition of a Lewis acid, i.e. an electron acceptor. These materials include clay substances such as attapulgite, bentonite and montmorillonite and treated clays such as silton clay as disclosed in U.S. Pat. Nos. 3,622,364 and 3,753,761, materials such as silica gel, talc, feldspar, magnesium trisilicate, pyrophyllite, zinc sulfate, zinc sulfide, calcium sulfate, calcium citrate, calcium phosphate, calcium fluoride and barium sulfate, aromatic carboxylic acids such as salicylic acid, derivatives of aromatic carboxylic acids and metal salts thereof as disclosed in U.S. Pat. No. 4,022,936 and acidic polymeric material such as phenol-formaldehyde polymers, phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof as disclosed in U.S. Pat. No. 3,672,935.

Particularly useful as acid color-activating substances are the metal-modified phenolic resins. Record sheet material coated with such resins is disclosed in U.S. Pat. No. 3,732,120. An example of the compositions which can be coated onto the surface of a sheet to react with the chromogenic compounds of this invention is as follows:

| Coating Composition | Percent by Weight |
| --- | --- |
| Zinc-modified phenolic polymer | 13.6 |
| Paper coating kaolin | 67.9 |
| Calcium carbonate | 6.0 |
| Styrene-butadiene latex | 6.0 |
| Etherified corn starch | 6.5 |

The following examples are given merely by illustrative of the present invention and are not to be considered as limiting.

The intermediates required for the preparation of the novel chromogenic compounds of this invention are classes of compounds readily obtained by procedures well known in the prior art.

The intermediates, substrate reactant B, which result in the indolizine radical portion of the novel chromogenic compounds can be made by procedures analogous to those in one or more of the following references:

1. T. Uchida and K. Matsumoto, Synthesis, 209(1976) and references therein.
2. N. P. Buu-Hoi et al., J. Org. Chem. 19, 1370(1954).
3. J. Fisher and J. Straley, British Pat. No. 1,159,691.
4. N. P. Buu-Hoi, Nguyen-Dat-Xuong and Ta-Thu-Cuc, Bull. Soc. Chim. France, 1277 (1966).
5. R. M. Palei and P. M. Kochergin, Khim. Geterotsikl. Soed. 536(1967)
6. F. Kroehnke and W. Zecher, Ber. 95, 1128(1962).
7. A. Druyhinina, P. Kochergin and N. Bychkove, Khim. Geterotshikl Soed., 856(1969).
8. F. Kroehnke and W. Friedrich, Ber. 96, 1195(1963).
9. G. W. H. Cheeseman and B. Tuck, J. Chem. Soc. 3678(1965).

The other reactant, the keto acid, required for the preparation of the novel chromogenic compounds of this invention is disclosed in U.S. Pat. No. 3,491,111, 3,491,112, 3,491,116, 3,509,173, 3,775, 424, 3,936,564, 4,020,068 and 4,022,771 and in Belgian Pat. No. 844,962.

Unless otherwise noted, the percentages throughout the application are by weight.

EXAMPLE 1

Preparation of 3-(1-ethyl-2-methylindol-3-yl)-3-(1-methyl-2-naphthylindolizin-3-yl)phthalide.

A mixture of 3.0 grams of (1-ethyl-2-methylindol-3-yl) (2-carboxyphenyl)ketone, 2.5 grams of 1-methyl-2-(2-naphthyl) indolizine and 10 ml. of acetic anhydride was heated at 39° C. for about two hours. The resulting solution was cooled and added to a mixture of ice, toluene and ammonia. The toluene layer was separated, dried, treated with charcoal and filtered. Petroleum ether was added and after fractional precipitation a crystalline product was obtained and recrystallized from a toluene-heptane mixture to a constant melting point of 191°-193° C. A chloroform solution of this final product gave a blue color when applied to a record sheet material coated with a zinc-modified phenolic resin.

EXAMPLE 2

Preparation of 3-(1-ethyl-2-methylindol-3-yl)-3-(1,2-diphenylindolizin-3-yl)phthalide.

A mixture of 3.06 grams of (1-ethyl-2-methylindol-3-yl) (2-carboxyphenyl)ketone, 2.7 grams of 2,3-diphenylindolizine and 10 ml. of acetic anhydride was heated at about 50° C. for 107 minutes. The reaction mixture was cooled and filtered and the obtained product was recrystallized from a toluene-heptane mixture. The 3.3 grams of product were recrystallized from a toluene-heptane mixture to a constant melting point of 227°-227.5° C. A chloroform solution of the product when applied to silica gel produced a blue color.

EXAMPLE 3

Preparation of 3-(1-ethyl-2-methylindol-3-yl)-3-(2,3-dimethylindolizin-1-yl)-4,5,6,7-tetrachlorophthalide.

A mixture of 4.3 grams of (1-ethyl-2-methylindol-3-yl) (2-carboxy-3,4,5,6-tetrachlorophenyl)ketone, 1.5 grams of 2,3-dimethylindolizine and 10 ml. of acetic anhydride was heated at 90° C. for about seven and one-half hours. The reaction mixture was cooled and filtered and the filtrate was extracted with toluene. The toluene extract was washed with cold dilute ammonia, concentrated and filtered. The 0.9 gram of material obtained was recrystallized from a toluene-heptane mixture to yield a product with a melting point of 227.5°-228° C. A solution of this material in chloroform yielded a purple color when applied to a record sheet material coated with a zinc-modified phenolic resin.

EXAMPLES 4-11

According to substantially the same procedures as described in any one of the Examples 1 to 3, an indolizine compound of the formula

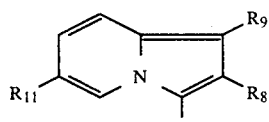

was mixed with an equimolar amount of (1-ethyl-2-methylindol-3-yl) (2-carboxyphenyl)ketone and about four to five grams of acetic anhydride were added per gram of reactant mixture. The reaction mixture was heated to 50°-60° C., poured over ice and adjusted to about pH 10 by the addition of ammonium hydroxide. The solid product was filtered and dried. A solution of the product in benzene or acetone was passed through a column of activated alumina to remove impurities. The solution was concentrated, the chromogenic material crystallized by the addition of heptane and the solid product was filtered and dried. In Table I are listed, respectively, the substituents on the indolizine reactant, the melting point and the color produced on silica gel by the resulting chromogenic compound product.

mixture was extracted with toluene. The toluene extract was passed through phase separation paper, concentrated on a steam bath, diluted with petroleum ether and filtered, yielding 1.7 grams of product. This material was recrystallized to a constant melting point of 223°-224° C. and a chloroform solution of the product gave a purple color when applied on a record sheet material coated with a zinc-modified phenolic resin or with silton clay.

EXAMPLE 13

Preparation of 3-(1-ethyl-2-methylindol-3-yl)-3-(2-phenyl-3-methyl-6-ethylindolizin-1-yl)-4-nitrophthalide.

A mixture of 1.7 grams of (1-ethyl-2-methylindol-3-yl) (2-carboxy-6-nitrophenyl)ketone, 1.2 grams of 2-phenyl-3-methyl-6-ethylindolizine and 10 ml. of acetic anhydride was heated at 52° C. for about 30 minutes. The reaction mixture was poured into a mixture of ice, toluene and ammonia. The toluene layer was separated and evaporated to dryness yielding 1.0 grams of oily product which was chromatographed on diatomaceous earth. Two fractions were obtained from the chromatography. One portion of 40 mg. had a melting point of 254° C. and the other portion of 10 mg. had a melting point of 225° C. Solutions of both produced purple colors on silica gel.

TABLE I

| | Indolizine Substituents | | | Melting Point | | |
|---|---|---|---|---|---|---|
| Example | $R_8$ | $R_9$ | $R_{11}$ | Darkens or Softens | Decomposition | Color on Silica Gel |
| 4. | –⟨phenyl⟩ | –CH₃ | H | 208° C. | 212°-216° C. | Blue |
| 5. | –⟨phenyl⟩ | H | H | 196° C. | 208°-212° C. | Blue |
| 6. | –⟨phenyl⟩ | H | –C₂H₅ | 145° C. | 200°-205° C. | Blue |
| 7. | –⟨phenyl⟩–OCH₃ | H | –C₂H₅ | 138° C. | 145°-150° C. | Blue |
| 8. | –⟨phenyl⟩–⟨phenyl⟩ | H | H | 165° C. | 171°-175° C. | Blue |
| 9. | –⟨phenyl⟩–OCH₃ | CH₃ | H | 170° C. | 145°-150° C. | Blue |
| 10. | –⟨phenyl⟩–OCH₃ | H | H | 115° C. | 165°-170° C. | Blue |
| 11. | –⟨phenyl⟩–Cl | H | H | 150° C. | 174°-178° C. | Blue |

EXAMPLE 12

Preparation of 3-(1-ethyl-2-methylindol-3-yl)-3-(2-phenyl-3-methyl-6-ethylindolizin-1-yl)phthalide.

A mixture of 1.5 grams of (1-ethyl-2-methylindol-3-yl) (2-carboxyphenyl)ketone, 1.2 grams of 2-phenyl-3-methyl-6-ethylindolizine and 10 ml of acetic anhydride was heated at 50° C. for about 30 minutes, the reaction product was poured into an ice-toluene mixture and the Additional experiments were performed where a keto acid and a substrate reactant B were mixed with acetic anhydride and heated. The reaction mixture was cooled, treated with dilute ammonium hydroxide and extracted with toluene. In Table II is a listing of the reactant pairs and the respective color produced when the toluene extract of the reaction product was applied to a record sheet material coated with a zinc-modified phenolic resin.

TABLE II

| Keto Acid | Substrate Reactant B | Color Produced |
|---|---|---|
| (1-ethyl-2-methylindol-3-yl) (2-carboxyphenyl)ketone | 2-methylindolizine | Purple |
| (1-ethyl-2-methylindol-3-yl) (2-carboxyphenyl)ketone | 2-phenyl-3-methylindolizine | Purple |
| (1-ethyl-2-methylindol-3-yl) (2-carboxyphenyl)ketone | 1,2-dimethylindolizine | Purple |

TABLE II-continued

| Keto Acid | Substrate Reactant B | Color Produced |
|---|---|---|
| (1-ethyl-2-methylindol-3-yl) (2-carboxyphenyl)ketone | 2-phenyl-5-methylindolizine | Purple |
| (1-ethyl-2-methylindol-3-yl) (2-carboxyphenyl)ketone | 2-(2-pyridyl)indolizine | Blue |
| (1-ethyl-2-methylindol-3-yl) (2-carboxy-3,4,5,6-tetrachlorophenyl)ketone | 2-methylindolizine | Blue |
| (1-ethyl-2-methylindol-3-yl) (2-carboxy-3,4,5,6-tetrachlorophenyl)ketone | 2-phenylindolizine | Blue |
| (1-ethyl-2-methylindol-3-yl) (2-carboxy-3,4,5,6-tetrachlorophenyl)ketone | 1-methyl-2-phenylindolizine | Blue |
| (1-ethyl-2-methylindol-3-yl) (2-carboxy-3,4,5,6-tetrachlorophenyl)ketone | 2-phenyl-3-methylindolizine | Blue |
| (1-ethyl-2-methylindol-3-yl) (2-carboxy-3,4,5,6-tetrachlorophenyl)ketone | 1-methyl-2-naphthylindolizine | Blue |
| (1-ethyl-2-methylindol-3-yl) (2-carboxy-3,4,5,6-tetrachlorophenyl)ketone | 1,2-diphenylindolizine | Green |
| (1-ethyl-2-methylindol-3-yl) (2-carboxy-3,4,5,6-tetrachlorophenyl)ketone | 1,2-dimethylindolizine | Red |
| (1,2-dimethylindol-3-yl) (2-carboxy-3-nitrophenyl)ketone | 2-phenyl indolizine | Blue |
| (1,2-dimethylindol-3-yl) (2-carboxy-3-nitrophenyl)ketone | 2-phenyl-5-methylindolizine | Purple |
| (1-methyl-2-phenylindol-3-yl) (2-carboxy-3-nitrophenyl)ketone | 1-methyl-2-phenylindolizine | Blue |
| (1-methyl-2-phenylindol-3-yl) (2-carboxy-3-nitrophenyl)ketone | 1-methyl-2-naphthylindolizine | Blue |
| (1-methyl-2-phenylindol-3-yl) (2-carboxy-3-nitrophenyl)ketone | 1,2-diphenylindolizine | Green |
| (1-methyl-2-phenylindol-3-yl) (2-carboxy-3-nitrophenyl)ketone | 1,2-dimethylindolizine | Blue |
| (1-methyl-2-phenylindol-3-yl) (2-carboxy-3-nitrophenyl)ketone | 2-phenyl-5-methylindolizine | Green |

EXAMPLE 14

Preparation of 3-(4-diethylamino-2-methoxyphenyl)-3-(2,3-dimethylindolizin-3-yl)phthalide.

A mixture of 3.3 grams of 2-methoxy-4-diethylamino-2-carboxybenzophenone, 1.5 grams of 2,3-dimethylindolizine and 10 ml. of acetic anhydride was heated at 40° C. for about one hour and then cooled in an ice bath. The resulting crystalline material was separated by filtration and recrystallized from heptane to yield 1.2 grams of product. This material was recrystallized three more times to yield a product with a constant melting point of 192.5°–193.5° C. A chloroform solution of the final product produced a blue color when applied to a record sheet material coated with a zinc-modified phenolic resin.

EXAMPLES 15–18

According to substantially the same procedure as described in Example 14, a keto acid was reacted with a substantially equimolar amount of a substrate reactor B in the presence of acetic anhydride with heating. The solid product was separated and recrystallized to a constant melting point. A solution of this product in chloroform was used to produce a color on a record sheet material coated with a zinc-modified phenolic resin or silton clay or on silica gel. These reactants and the results obtained are listed in Table III.

TABLE III

| Example | Keto Acid | Substrate Reactant B | Yield | Melting Color | Color Produced Color | Color Produced Acid Reactant |
|---|---|---|---|---|---|---|
| 15 | 2-carboxy-4,4'-bis(dimethylamino)benzophenone | 1-methyl-2-phenyl-indolizine | 44% | 171–172° C. | Blue | zinc-modified phenolic resin |
| 16 | 2-methoxy-4-diethylamino-2'-carboxybenzophenone | 1-methyl-2-phenyl-indolizine | 37% | 206–208° C. | Blue | zinc-modified phenolic resin |
| 17 | 2-ethoxy-4-diethylamino-2'-carboxybenzophenone | 2-(2,5-dimethoxyphenyl)-indolizine | 95% | 95–98° C. | Green | silton clay |
| 18 | 2-carboxy-4,4'-bis(dimethylamino)benzophenone | 2-phenyl-3-methyl-6-ethylindolizine | | 226–228° C. | Purple | silica gel |
| 19 | 2-carboxy-4,4'-bis(dimethylamino)benzophenone | 2-phenyl-3-methyl-indolizine | 16% | 193–194° C. | Blue | zinc-modified phenolic resin |
| 20 | 2-carboxy-4,4'-bis(dimethylamino)benzophenone | 1-methyl-2-(2-naphthyl)-indolizine | 89% | 217–220° C. | Blue | zinc-modified phenolic resin |
| 21 | 2-carboxy-4,4'-bis(dimethylamino)benzophenone | 2-(2-pyridyl)-indolizine | 61% | 196.5–197.0° C. | Blue-Green | zinc-modified phenolic resin |
| 22 | 2-carboxy-4,4'-bis(dimethylamino)benzophenone | 1-phenyl-2-(2-pyridyl)-indolizine | 5% | 245–246° C. | Blue-Green | zinc-modified phenolic resin |

Additional experiments were performed where a keto acid and a substrate reactor B were mixed with acetic anhydride and heated. The reaction mixture was cooled, treated with dilute ammonium hydroxide and extracted with toluene. In Table IV is a listing of the reactant pairs and the respective color produced when the toluene extract of the reaction product was applied to a record sheet material coated with a zinc-modified phenolic resin.

TABLE IV

| Keto Acid | Substrate Reactant B | Color Produced |
|---|---|---|
| 4'-diethylamino-2-carboxybenzophenone | 2-methylindolizine | Blue-Green |
| 4'-diethylamino-2-carboxybenzophenone | 2-phenylindolizine | Blue |
| 4'-diethylamino-2-carboxybenzophenone | 1-methyl-2-phenylindolizine | Blue-Green |
| 4'-diethylamino-2-carboxybenzophenone | 2-phenyl-3-methylindolizine | Blue |
| 4'-diethylamino-2-carboxybenzophenone | 1,2-diphenylindolizine | Green |
| 4'-diethylamino-2-carboxybenzophenone | 2-phenyl-3-methyl-6-ethylindolizine | Blue |
| 4'-diethylamino-2-carboxybenzophenone | 2-phenyl-5-methylindolizine | Blue-Green |
| 4'-diethylamino-2-carboxy-3,4,5,6-tetrachlorobenzophenone | 2-methylindolizine | Green |
| 4'-diethylamino-2-carboxy-3,4,5,6-tetrachlorobenzophenone | 2-phenylindolizine | Green |
| 4'-diethylamino-2-carboxy-3,4,5,6-tetrachlorobenzophenone | 1-methyl-2-phenylindolizine | Green |
| 4'-diethylamino-2-carboxy-3,4,5,6-tetrachlorobenzophenone | 2-phenyl-3-methylindolizine | Green |
| 4'-diethylamino-2-carboxy-3,4,5,6-tetrachlorobenzophenone | 1,2-diphenylindolizine | Green |
| 4'-diethylamino-2-carboxy-3,4,5,6-tetrachlorobenzophenone | 2-phenyl-3-methyl-6-ethylindolizine | Green |
| 4'-diethylamino-2-carboxy-3,4,5,6-tetrachlorobenzophenone | 2-phenyl-5-methylindolizine | Green |
| 2-carboxy-4,4'-bis(dimethylamino)benzophenone | 2-methylindolizine | Blue |
| 2-carboxy-4,4'-bis(dimethylamino)benzophenone | 2-phenylindolizine | Blue |
| 2-carboxy-4,4'-bis(dimethylamino)benzophenone | 2-phenyl-3-methylindolizine | Purple |
| 2-carboxy-4,4'-bis(dimethylamino)benzophenone | 1,2-diphenylindolizine | Blue |
| 2-carboxy-4,4'-bis(dimethylamino)benzophenone | 2-phenyl-3-methyl-6-ethylindolizine | Purple |
| 2-carboxy-4,4'-bis(dimethylamino)benzophenone | 2-phenyl-5-methylindolizine | Purple |
| 2-carboxy-4,4'-bis(dimethylamino)benzophenone | 2-methyl-3-phenylindolizine | Blue |
| 2-carboxy-4,4'-bis(dimethylamino)benzophenone | 2-(2-pyridyl)indolizine | Blue |
| 2-carboxy-2'-methoxy-4'-methyl-N-p-tolylaminobenzophenone | 2-methylindolizine | Blue |
| 2-carboxy-2'-methoxy-4'-methyl-N-p-tolylaminobenzophenone | 2-phenylindolizine | Blue |
| 2-carboxy-2'-methoxy-4'-methyl-N-p-tolylaminobenzophenone | 1-methyl-2-phenylindolizine | Blue-Green |
| 2-carboxy-2'-methoxy-4'-methyl-N-p-tolylaminobenzophenone | 2-phenyl-3-methylindolizine | Blue |
| 2-carboxy-2'-methoxy-4'-methyl-N-p-tolylaminobenzophenone | 1,2-diphenylindolizine | Green |
| 2-carboxy-2'-methoxy-4'-methyl-N-p-tolylaminobenzophenone | 2-phenyl-5-methylindolizine | Blue |
| 2-carboxy-3,4,5,6-tetrachloro-2'-methoxy-4'-diethylaminobenzophenone | 2-methylindolizine | Green |
| 2-carboxy-3,4,5,6-tetrachloro-2'-methoxy-4'-diethylaminobenzophenone | 2-phenylindolizine | Green |
| 2-carboxy-3,4,5,6-tetrachloro-2'-methoxy-4'-diethylaminobenzophenone | 1-methyl-2-phenylindolizine | Green |
| 2-carboxy-3,4,5,6-tetrachloro-2'-methoxy-4'-diethylaminobenzophenone | 2-phenyl-3-methylindolizine | Green |
| 2-carboxy-3,4,5,6-tetrachloro-2'-methoxy-4'-diethylaminobenzophenone | 1,2-diphenylindolizine | Green |
| 2-carboxy-3,4,5,6-tetrachloro-2'-methoxy-4'-diethylaminobenzophenone | 2-phenyl-3-methyl-6-ethylindolizine | Green |
| 2-carboxy-3,4,5,6-tetrachloro-2'-methoxy-4'-diethylaminobenzophenone | 2-phenyl-5-methylindolizine | Green |
| 2-carboxy-2'-methoxy-4'-cyclohexylaminobenzophenone | 2-methylindolizine | Blue-Green |
| 2-carboxy-2'-methoxy-4'-cyclohexylaminobenzophenone | 2-phenyl-3-methylindolizine | Blue |
| 2-carboxy-2'-methoxy-4'-cyclohexylaminobenzophenone | 1,2-diphenylindolizine | Green |
| 2-carboxy-2'-methoxy-4'-cyclohexylaminobenzophenone | 2-phenyl-3-methyl-6-ethylindolizine | Green |
| 2-carboxy-2'-methoxy-4'-cyclohexylaminobenzophenone | 2-phenyl-5-methylindolizine | Blue |
| 2-carboxy-2'-n-butoxy-4'-diethylaminobenzophenone | 1-methyl-2-phenylindolizine | Green |
| 2-carboxy-2'-n-butoxy-4'-diethylaminobenzophenone | 2-phenyl-3-methylindolizine | Blue |
| 2-carboxy-2'-n-butoxy-4'-diethylaminobenzophenone | 1,2-diphenylindolizine | Green |
| 2-carboxy-2'-n-butoxy-4'-diethylaminobenzophenone | 2-phenyl-3-methyl-6-ethylindolizine | Blue |
| 2-carboxy-2'-n-butoxy-4'-diethylaminobenzophenone | 2-phenyl-5-methylindolizine | Green |
| 2-carboxy-4'-morpholinobenzophenone | 1-methyl-2-phenylindolizine | Blue |
| 2-carboxy-4'-morpholinobenzophenone | 2-phenyl-3-methylindolizine | Blue |
| 2-carboxy-4'-morpholinobenzophenone | 1,2-diphenylindolizine | Blue |
| 2-carboxy-4'-morpholinobenzophenone | 2-phenyl-3-methyl-6-ethylindolizine | Blue |
| 2-carboxy-4'-morpholinobenzophenone | 2-phenyl-5-methylindolizine | Blue |
| 2-carboxy-2'-methoxy-4'-diethylaminobenzophenone | 2-methylindolizine | Blue-Green |
| 2-carboxy-2'-methoxy-4'-diethylaminobenzophenone | 2-phenylindolizine | Green |
| 2-carboxy-2'-methoxy-4'-diethylaminobenzophenone | 2-phenyl-3-methylindolizine | Blue |
| 2-carboxy-2'-methoxy-4'-diethylaminobenzophenone | 1,2-diphenylindolizine | Green |
| 2-carboxy-2'-methoxy-4'-diethylaminobenzophenone | 2-phenyl-3-methyl-6-ethylindolizine | Blue |
| 2-carboxy-2'-methoxy-4'-diethylaminobenzophenone | 2-phenyl-5-methylindolizine | Blue-Green |
| 2-carboxy-2'-methoxy-4'-diethylaminobenzophenone | 2-methyl-3-phenylindolizine | Green |
| 2-carboxy-2'-methoxy-4'-diethylaminobenzophenone | 2-(2-pyridyl)indolizine | Green |

In the examples to follow which disclose the preparation of chromogenic compounds of the pyridinone and

EXAMPLE 23

Preparation of 7-(1-ethyl-2-methylindol-3-yl)-7-(1,2-diphenylindolizin-3-yl)-5,7-dihydrofuro[3,4-b]pyridin-5-one.

A mixture of 1.6 grams of (1-ethyl-2-methylindol-3-yl)(3-carboxypyridin-2-yl)ketone, 1.85 grams of 1,2-diphenylindolizine and 10 ml. of acetic anhydride was heated at about 40° C. for 104 minutes and then cooled in an ice bath. The reaction mixture was filtered and the product was repeatedly recrystallized from a toluene-petroleum ether mixture until a constant melting point of 206.5°–207.5° C. was obtained. A chloroform solution of the final product produced a blue color when applied to a record sheet material coated with a zinc-modified phenolic resin.

EXAMPLES 24–28

According to substantially the same procedure as described in Example 23, (1-ethyl-2-methylindol-3-yl)(3-carboxypyridin-2-yl)ketone was reacted with a substantially equimolar amount of substrate reactant B in the presence of acetic anhydride with heating. The reaction product was separated and recrystallized to a constant melting point. A solution of each product was used to produce a color on record sheet material coated with a zinc-modified phenolic resin. These reactants and the results obtained are listed in Table V.

TABLE V

| Example | Substrate Reactant B | Yield | Melting Point | Color on zinc-modified phenolic resin record sheet |
|---|---|---|---|---|
| 24 | 2,3-dimethylindolizine | 69% | 218–219° C. | Blue |
| 25 | 2-phenylindolizine | 33% | 200–201° C. | Blue |
| 26 | 2-(p-dimethylaminophenyl)indolizine | 37% | | Blue |
| 27 | 2-phenyl-3-methylindolizine | | 226–227.5° C. | Blue |
| 28 | 2-phenyl-3-methyl-6-ethylindolizine | | | Purple |

Additional experiments were performed where a keto acid and a substrate reactant B were mixed with acetic anhydride and heated. The reaction mixture was cooled, treated with dilute ammonium hydroxide and extracted with toluene. In Table VI is a listing of the reactant pairs and the respective color produced when the toluene extract of the reaction product was applied to a record sheet material coated with zinc-modified phenolic resin.

TABLE VI

| Keto Acid | Substrate Reactant B | Color Produced |
|---|---|---|
| (1-ethyl-2-methylindol-3-yl)(3-carboxypyridin-2-yl)ketone | 2-methylindolizine | Purple |
| (1-ethyl-2-methylindol-3-yl)(3-carboxypyridin-2-yl)ketone | 1-methyl-2-phenylindolizine | Blue |
| (1-ethyl-2-methylindol-3-yl)(3-carboxypyridin-2-yl)ketone | 2-phenyl-3-methylindolizine | Blue |
| (1-ethyl-2-methylindol-3-yl)(3-carboxypyridin-2-yl)ketone | 1-methyl-2-naphthylindolizine | Blue |
| (1-ethyl-2-methylindol-3-yl)(3-carboxypyridin-2-yl)ketone | 1,2-dimethylindolizine | Purple |
| (1-ethyl-2-methylindol-3-yl)(3-carboxypyridin-2-yl)ketone | 2-phenyl-5-methylindolizine | Blue |
| (1-ethyl-2-methylindol-3-yl)(3-carboxypyridin-2-yl)ketone | 2-methyl-3-phenylindolizine | Purple |
| (1-ethyl-2-methylindol-3-yl)(3-carboxypyridin-2-yl)ketone | 2-(2-pyridyl)indolizine | Blue |
| (1,2-dimethylindol-3-yl)(3-carboxypyridin-4-yl)ketone | 2-methylindolizine | Purple |
| (1,2-dimethylindol-3-yl)(3-carboxypyridin-4-yl)ketone | 2-phenyl-3-methylindolizine | Purple |
| (1,2-dimethylindol-3-yl)(3-carboxypyridin-4-yl)ketone | 1,2-diphenylindolizine | Purple |
| (1,2-dimethylindol-3-yl)(3-carboxypyridin-4-yl)ketone | 1,2-dimethylindolizine | Red |
| (1-isopentyl-2-methylindol-3-yl)(3-carboxypyridin-2-yl)ketone | 1-methyl-2-phenylindolizine | Blue |
| (1-isopentyl-2-methylindol-3-yl)(3-carboxypyridin-2-yl)ketone | 1-methyl-2-naphthylindolizine | Blue |
| (1-isopentyl-2-methylindol-3-yl)(3-carboxypyridin-2-yl)ketone | 1,2-diphenylindolizine | Blue-Green |
| (1-isopentyl-2-methylindol-3-yl)(3-carboxypyridin-2-yl)ketone | 1,2-dimethylindolizine | Purple |
| (1-isopentyl-2-methylindol-3-yl)(3-carboxypyridin-2-yl)ketone | 2-phenyl-5-methylindolizine | Blue |

EXAMPLE 29

Preparation of 5-(4-diethylamino-2-ethoxyphenyl)-5-(2-(2,5-dimethoxyphenyl)indolizin-3-yl)-5,7-dihydrofuro[3,4-b]pyridin-7-one.

A solution of 0.50 grams of 2-(2,5-dimethoxyphenyl)indolizine and 0.68 grams of (4-diethylamino-2-ethoxyphenyl)(3-carboxypyridin-2-yl)ketone in 15 ml. of acetic anhydride was heated 2 hours at 50° C. The solution was poured into 150 ml. of water, adjusted to pH 9.8 with ammonium hydroxide and stirred one hour. A benzene extraction was made. Evaporation of the dried benzene extract under reduced pressure left 1.13 grams of product. The infrared spectrum showed a strong lactone carbonyl peak at 1775 cm$^{-1}$. Thin layer chromatography showed a predominant green spot and a smaller bluish spot. A chloroform solution of the product produced a green color on a record sheet material coated with a zinc-modified phenolic resin or with silton clay.

EXAMPLES 30-35

According to substantially the same procedure as disclosed in Example 29, (4-diethylamino-2-ethoxyphenyl)(3-carboxypyridin-2-yl)ketone was reacted with a substantially equimolar amount of substrate reactant B in the presence of acetic anhydride and with heating. The reaction product was isolated and a chloroform solution of each product was used to produce a color on record sheet material coated with a zinc-modified phenolic resin. The results are listed in Table VII.

TABLE VII

| Example | Substrate Reactant B | Infrared Spectrum Peak | Melting Point | Color on zinc-modified phenolic resin record sheet |
|---|---|---|---|---|
| 30 | 5-methyl-2-(2,5-dimethoxyphenyl)indolizine | 1755 cm$^{-1}$ | 122-124° C. | Blue |
| 31 | 2-(p-dimethylaminophenyl)indolizine | 1765 cm$^{-1}$ | | Green |
| 32 | 2-phenyl-3-methyl-6-ethylindolizine | | | Blue-Green |
| 33 | 2-phenylindolizine | | | Green |
| 34 | 2-phenyl-3-methylindolizine | | | Green |
| 35 | 1-methyl-2-phenylindolizine | | | Green |

Additional experiments were performed where a keto acid and a substrate reactant B were mixed with acetic anhydride and heated. The reaction mixture was cooled, treated with dilute ammonium hydroxide and extracted with toluene. In Table VIII is a listing of the reactant pairs and the respective color produced when the toluene extract of the reaction product was applied to a record sheet material coated with a zinc-modified phenolic resin.

TABLE VIII

| Keto Acid | Substrate Reactant B | Color Produced |
|---|---|---|
| (4-diethylamino-2-ethoxyphenyl)(3-carboxypyridin-2-yl)ketone | 1,2-diphenylindolizine | Green |
| (4-diethylamino-2-ethoxyphenyl)(3-carboxypyridin-2-yl)ketone | 2,3-dimethylindolizine | Blue |
| (4-diethylamino-2-ethoxyphenyl)(3-carboxypyridin-2-yl)ketone | 2-phenyl-3-methyl-6-ethylindolizine | Blue |
| (4-diethylamino-2-ethoxyphenyl)(3-carboxypyridin-2-yl)ketone | 2-(p-chlorophenyl)indolizine | Green |
| (4-diethylamino-2-ethoxyphenyl)(3-carboxypyridin-2-yl)ketone | 2-(2-pyridyl)indolizine | Green |
| (1-methyl-1,2,3,4-tetrahydroquinolin-6-yl)-(3-carboxypyridin-2-yl)ketone | 1-methyl-2-phenylindolizine | Green |
| (1-methyl-1,2,3,4-tetrahydroquinolin-6-yl)-(3-carboxypyridin-2-yl)ketone | 2-phenyl-3-methylindolizine | Blue Green |
| (1-methyl-1,2,3,4-tetrahydroquinolin-6-yl)-(3-carboxypyridin-2-yl)ketone | 1-methyl-2-naphthylindolizine | Green |
| (1-methyl-1,2,3,4-tetrahydroquinolin-6-yl)-(3-carboxypyridin-2-yl)ketone | 1,2-diphenylindolizine | Green |
| (1-methyl-1,2,3,4-tetrahydroquinolin-6-yl)-(3-carboxypyridin-2-yl)ketone | 2,3-dimethylindolizine | Blue |
| (1-methyl-1,2,3,4-tetrahydroquinolin-6-yl)-(3-carboxypyridin-2-yl)ketone | 2-phenyl-5-methylindolizine | Blue-Green |
| (2,3,6,7-tetrahydro-1H,5H-benzo[ij]-quinolizin-9-yl)(3-carboxypyridin-2-yl)ketone | 2-phenylindolizine | Green |
| (2,3,6,7-tetrahydro-1H,5H-benzo[ij]-quinolizin-9-yl)(3-carboxypyridin-2-yl)ketone | 1-methyl-2-(p-methoxyphenyl)indolizine | Green |
| (2,3,6,7-tetrahydro-1H,5H-benzo[ij]-quinolizin-9-yl)(3-carboxypyridin-2-yl)ketone | 2-phenyl-3-methyl-6-ethylindolizine | Green |
| (2,3,6,7-tetrahydro-1H,5H-benzo[ij]-quinolizin-9-yl)(3-carboxypyridin-2-yl)ketone | 2-(p-chlorophenyl)indolizine | Green |
| (2,3,6,7-tetrahydro-1H,5H,benzo[ij]-quinolizin-9-yl)(3-carboxypyridin-2-yl)ketone | 2-(2,5-dimethoxyphenyl)indolizine | Green |
| (2,3,6,7-tetrahydro-1H,5H-benzo[ij]-quinolizin-9-yl)(3-carboxypyridin-2-yl)ketone | 2-(p-methoxyphenyl)indolizine | Green |

EXAMPLE 36

Preparation of 3-(1-ethyl-2-methylindol-3-yl)-3-(1-methyl-2-phenylindolizin-3-yl)-1,3-dihydrofuro[3,4-b]quinolin-1-one.

A mixture of 3.4 grams of (1-ethyl-2-methylindol-3-yl)(3-carboxyquinolin-2-yl)ketone, 2.1 grams of 1-methyl-2-phenylindolizine and 10 ml. of acetic anhydride was heated at 40° C. for 118 minutes and poured into a mixture of ice, toluene and ammonia. The toluene portion was separated, concentrated to about 150 ml., treated with charcoal and filtered. Enough petroleum ether was added to make one liter and a red dye impurity was filtered off. The next day, crystalline material was filtered and recrystallized from a toluene-petroleum ether mixture yielding a product with a melting point of 198°–199° C. A solution of the product in chloroform when applied to record sheet material coated with a zinc-modified phenolic resin produced a blue color.

Additional experiments were performed where a keto-acid and a substrate reactant B were mixed with acetic anhydride and heated. The reaction mixture was cooled, treated with dilute ammonium hydroxide and extracted with toluene. In Table IX is a listing of the reaction pairs and the respective color produced when the toluene extract of the reaction product was applied to a record sheet material coated with a zinc-modified phenolic resin.

cooled, treated with dilute ammonium hydroxide and extracted with toluene. In Table X is a listing of the reactant pairs and the respective color produced when the toluene extract of the reaction product was applied to a record sheet material coated with a zinc-modified phenolic resin.

TABLE X

| Keto Acid | Substrate Reactant B | Color Produced |
| --- | --- | --- |
| (4-diethylamino-2-ethoxyphenyl)(3-carboxyquinolin-2-yl)ketone | 2-phenylindolizine | Green |
| (4-diethylamino-2-ethoxyphenyl)(3-carboxyquinolin-2-yl)ketone | 1-methyl-2-phenylindolizine | Green |
| (4-diethylamino-2-ethoxyphenyl)(3-carboxyquinolin-2-yl)ketone | 2-phenyl-3-methylindolizine | Blue |
| (4-diethylamino-2-ethoxyphenyl)(3-carboxyquinolin-2-yl)ketone | 1-methyl-2-naphthylindolizine | Green |
| (4-diethylamino-2-ethoxyphenyl)(3-carboxyquinolin-2-yl)ketone | 2,3-dimethylindolizine | Blue |
| (4-diethylamino-2-ethoxyphenyl)(3-carboxyquinolin-2-yl)ketone | 2-phenyl-3-methyl-6-ethylindolizine | Blue |
| (4-diethylamino-2-ethoxyphenyl)(3-carboxyquinolin-2-yl)ketone | 2-(p-chlorophenyl)indolizine | Green |
| (4-diethylamino-2-ethoxyphenyl)(3-carboxyquinolin-2-yl)ketone | 2-(p-methoxyphenyl)indolizine | Green |

TABLE IX

| Keto Acid | Substrate Reactant B | Color Produced |
| --- | --- | --- |
| (1-ethyl-2-methylindol-3-yl)(3-carboxyquinolin-2-yl)ketone | 2-phenylindolizine | Blue |
| (1-ethyl-2-methylindol-3-yl)(3-carboxyquinolin-2-yl)ketone | 2-phenyl-3-methylindolizine | Blue |
| (1-ethyl-2-methylindol-3-yl)(3-carboxyquinolin-2-yl)ketone | 1-methyl-2-naphthylindolizine | Blue |
| (1-ethyl-2-methylindol-3-yl)(3-carboxyquinolin-2-yl)ketone | 1,2-dimethylindolizine | Blue |
| (1-ethyl-2-methylindol-3-yl)(3-carboxyquinolin-2-yl)ketone | 2-phenyl-5-methylindolizine | Blue |
| (1-ethyl-2-methylindol-3-yl)(3-carboxyquinolin-2-yl)ketone | 2-methyl-3-phenylindolizine | Blue |

EXAMPLE 37

Preparation of 3-(4-diethylamino-2-ethoxyphenyl)-3-(1,2-diphenylindolizin-3-yl)-1,3-dihydrofuro[3,4-b]quinolin-1-one.

A mixture of 2.0 grams of (4-diethylamino-2-ethoxyphenyl)(3-carboxyquinol-2-yl)ketone, 1.4 grams of 1,2-diphenylindolizine and 10 ml. of acetic anhydride was stirred at room temperature for an hour. The mixture was scratched, the resultant precipitate was filtered off and 2.5 grams of product were collected. The product was repeatedly recrystallized to a constant melting point of 265°–266° C. A solution of the product applied to a record sheet material coated with a zinc-modified phenolic resin produced a green color.

Additional experiments were performed where a keto-acid and a substrate reactant B were mixed with acetic anhydride and heated. The reaction mixture was cooled, treated with dilute ammonium hydroxide and

EXAMPLE 38

Preparation of 7-(2-phenyl-3-methyl-6-ethylindolizin-1-yl)-7-(1-ethyl-2-methylindol-3-yl)-5,7-dihydrofuro[3,4-b]pyrazin-5-one.

A mixture of 3.1 grams of (1-ethyl-2-methylindol-3-yl)(2-carboxypyrazin-3-yl)ketone, 2.4 grams of 2-phenyl-3-methyl-6-ethylindolizine and 25 ml. of acetic anhydride was stirred at room temperature for about 1½ hours. The reaction mixture was poured into a mixture of ice and toluene and the mixture was made basic by the addition of cold ammonium hydroxide. The toluene portion was separated, dried with phase separation paper, concentrated, diluted with petroleum ether and chromatographed on alumina. The impurities were eluted with toluene and ethyl acetate. The portion of the alumina column containing the product was removed and the product was eluted from the alumina with methanol. The methanol was evaporated, the resulting solid was dissolved in toluene and petroleum ether was added. After standing several days the solution was filtered and the filtrate evaporated to a yield 0.1 gram of product. A solution of the product when applied to silica gel or a record sheet material coated with a zinc-modified phenolic resin or silton clay produced a blue color.

Additional experiments were performed where a keto acid and a substrate reactant B were mixed with acetic anhydride and heated. The reaction mixture was cooled, treated with dilute ammonium hydroxide and extracted with toluene. In Table XI is a listing of the reactant pairs and the respective color produced when the toluene extract of the reaction product was applied to a record sheet material coated with a zinc-modified phenolic resin.

TABLE XI

| Keto Acid | Substrate Reactant B | Color Produced |
|---|---|---|
| (1-ethyl-2-methylindol-3-yl)(2-carboxypyrazin-3-yl)ketone | 2-phenylindolizine | Blue |
| (1ethyl-2-methylindol-3-yl)(1-carboxypyrazin-3-yl)ketone | 1-methyl-2-phenylindolizine | Blue |
| (1-ethyl-1-methylindol-3-yl)(2-carboxypyrazin-3-yl)ketone | 2-phenyl-3-methylindolizine | Blue |
| (1-ethyl-2-methylindol-3-yl)(2-carboxypyrazin-3-yl)ketone | 1-methyl-2-naphthylindolizine | Blue-Green |
| (1-ethyl-2-methylindol-3-yl)(2-carboxypyrazin-3-yl)ketone | 1,2-diphenylindolizine | Blue |
| (2-ethyl-2-methylindol-3-yl)(2-carboxypyrazin-3-yl)ketone | 2-methyl-3-phenylindolizine | Blue |

EXAMPLE 39

Preparation of 1-(1-ethyl-2-methylindol-3-yl)-1-(2-phenyl-3-methylindolizin-1-)1,3-dihydrofuro[3,4-b]quinoxalin-3-one.

A mixture of 3.6 grams of (1-ethyl-2-methylindol-3-yl)(3-carboxyquinoxalin-2-yl)ketone, 2.0 grams of 2-phenyl-3-methylindolizine and 10 ml. of acetic anhydride was heated at 35°-36° C. for 45 minutes. The reaction mixture was poured into a mixture of ice, ammonia and toluene. The toluene portion was separated and concentrated yielding 0.9 grams of material which was recrystallized twice from toluene-petroleum ether. The final product had a melting point of 188°-189° C. A solution of the product when applied to a record sheet material coated with a zinc-modified phenolic resin produced a blue color.

Additional experiments were performed where a keto-acid and a substrate reactant B were mixed with acetic anhydride and heated. The reaction mixture was cooled, treated with dilute ammonium hydroxide and extracted with toluene. In Table XII is a listing of the reactant pairs and the respective color produced when the toluene extract of the reaction product was applied to a record sheet material coated with a zinc-modified phenolic resin.

TABLE XII

| Keto Acid | Substrate Reactant B | Color Produced |
|---|---|---|
| (1-ethyl-2-methylindol-3-yl) (3-carboxyquinoxalin-2-yl)ketone | 2-phenylindolizine | Blue |
| (1-ethyl-2-methylindol-3-yl) (3-carboxyquinoxalin-2-yl)ketone | 1-methyl-2-phenylindolizine | Blue-Black |
| (1-ethyl-2-methylindol-3-yl) (3-carboxyquinoxalin-2-yl)ketone | 1-methyl-2-naphthylindolizine | Blue-Black |
| (1-ethyl-2-methylindol-3-yl) (3-carboyquinoxalin-2-yl)ketone | 1,2-diphenylinolizine | Blue-Black |
| (1-ethyl-2-methylindol-3-yl) (3-carboxyquinoxalin-2-yl)ketone | 2-methyl-3-phenylindolizine | Purple |
| (4-diethylamino-2-ethoxyphenyl) (3-carboxyquinoxalin-2-yl)ketone | 1-methyl-2-phenylindolizine | Green |
| (4-diethylamino-2-ethoxyphenyl) (3-carboxyquinoxalin-2-yl)ketone | 2-phenyl-3-methylindolizine | Green |
| (4-diethylamino-2-ethoxyphenyl) (3-carboxyquinoxalin-2-yl)ketone | 1-methyl-2-naphthylindolizine | Green |
| (4-diethylamino-2-ethoxyphenyl) (3-carboxyquinoxalin-2-yl)ketone | 1,2-diphenylindolizine | Green |
| (4-diethylamino-2-ethoxyphenyl) (3-carboxyquinoxalin-2-yl)ketone | 2,3-dimethylindolizine | Blue-Green |
| (4-diethylamino-2-ethoxyphenyl) (3-carboxyquinoxalin-2-yl)ketone | 2-phenyl-5-methylindolizine | Blue-Green |
| (4-diethylamino-2-chlorophenyl) (3-carboxyquinoxalin-2-yl)ketone | 1-methyl-2-phenylindolizine | Green-Black |
| (4-diethylamino-2-chlorophenyl) (3-carboxyquinoxalin-2-yl)ketone | 2-phenyl-3-methylindolizine | Blue |
| (4-diethylamino-2-chlorophenyl) (3-carboxyquinoxalin-2-yl)ketone | 1,2-diphenylindolizine | Green |
| (4-diethylamino-2-chlorophenyl) (3-carboxyquinoxalin-2-yl)ketone | 2,3-dimethylindolizine | Blue-Green |
| (4-diethylamino-2-chlorophenyl) (3-carboxyquinoxalin-2-yl)ketone | 2-phenyl-3-methyl-6-ethylindolizine | Blue-Black |
| (4-diethylamino-2-chlorophenyl) (3-carboxyquinoxalin-2-yl)ketone | 2-methyl-3-phenylindolizine | Green |

The chromogenic compound Examples identified in Table XIII were subjected to elemental analysis. The molecular formula, the calculated analysis based on the molecular formula and the results found on analysis are listed in the table.

TABLE XIII

| Ex. | Molecular Formula | Calculated Analysis | | | | | Found on Analysis | | | | |
|---|---|---|---|---|---|---|---|---|---|---|---|
| | | C | H | N | O | Cl | C | H | N | O | Cl |
| 1 | $C_{38}H_{30}N_2O_2$ | 83.23% | 5.72% | 4.94% | | | 83.49% | 5.53% | 5.12% | | |
| 2 | $C_{39}H_{30}N_2O_2$ | 83.83% | 5.41% | 5.01% | | | 83.93% | 5.50% | 4.91% | | |
| 3 | $C_{29}H_{22}N_2Cl_4O_2$ | 60.86% | 3.88% | 4.90% | | 24.78% | 60.93% | 3.92% | 4.83% | | 24.80% |
| 14 | $C_{29}H_{30}N_2O_3$ | 76.63% | 6.65% | 6.16% | | | 76.84% | 6.66% | 6.05% | | |
| 15 | $C_{33}H_{31}N_3O_2$ +$C_7H_8$ (1 mole toluene) | 80.91% | 6.62% | 7.08% | | | 81.12% | 6.73% | 7.12% | | |
| 16 | $C_{34}H_{32}N_2O_3$ | 79.04% | 6.24% | 5.42% | | | 79.22% | 6.35% | 5.35% | | |
| 23 | $C_{38}H_{29}N_3O_2$ | 81.55% | 5.22% | 7.51% | | | 81.50% | 5.36% | 7.48% | | |
| 24 | $C_{28}H_{25}N_3O_2$ | 77.22% | 5.79% | 9.65% | | | 77.40% | 5.91% | 9.60% | | |
| 25 | $C_{32}H_{25}N_3O_2$ | 79.48% | 5.21% | 8.69% | | | 79.28% | 5.30% | 8.43% | | |
| 30 | $C_{36}H_{37}N_3O_2$ | 73.07% | 6.30% | 7.10% | 13.52% | | 73.18% | 6.47% | 6.82% | 13.45% | |
| 36 | $C_{36}H_{29}N_3O_2$ | 80.72% | 5.46% | 7.84% | | | 80.87% | 5.48% | 7.63% | | |
| 39 | $C_{36}H_{28}N_4O_2$ | 78.81% | 5.14% | 10.21% | | | 78.60% | 5.27% | 10.31% | | |

Preparation of pressure sensitive copy paper.

Solutions of three chromogenic compounds of the present invention were individually microencapsulated according to U.S. Pat. No. 4,100,103. The microcapsules were mixed with additives, and the mixture was coated and dried to produce a pressure sensitive transfer sheet.

EXAMPLE 40

A 1.7% solution of the chromogenic compound of Example 4 in a 64:36 weight ratio solvent mixture of ethyldiphenylmethane (U.S. Pat. No. 3,996,405) and saturated hydrocarbon oil (distillation range: 370°–500° F.) was prepared. A solution was made of a mixture of 50 grams of a 10% water solution of EMA-31 [poly-(ethylene-co-maleic anhydride), sold by Monsanto Company] and 100 grams of water, the pH of the solution was adjusted to 4 with 20% sodium hydroxide and 25 grams of Resimene 714 (an 80% solution of methylated methylol melamine in water sold by Monsanto Company) was added. Into this aqueous solution was emulsified the above chromogenic compound solution to an oil drop size of predominantly less than 10 microns. This emulsion was placed with stirring in a 55° C. water bath. After at least 30 minutes, heating of the bath was discontinued and the microcapsule batch continued to stir in the cooling bath overnight.

The following mixture was prepared, dispersed in a blender, coated on a paper substrate with a #12 wire-wound coating rod and dried:
- 100 grams of above microcapsule slurry
- 120 grams of water
- 10 grams of uncooked wheat starch
- 40 grams of 10% Penford Gum 230 (modified corn starch binder)

EXAMPLE 41

In a similar manner to Example 40, a 1.7% solution of the chromogenic compound of Example 5 was encapsulated and the microcapsules coated to produce a pressure sensitive transfer sheet.

EXAMPLE 42

In a similar manner to Example 40, a 1.7% solution of the chromogenic compound of Example 25 was encapsulated and the microcapsules coated to produce a pressure sensitive transfer sheet.

The three pressure sensitive transfer sheets (CB sheets) of Examples 40, 41 and 42 were tested face to face with underlying receiving sheets (CF sheets), each bearing a coating comprising an oil-soluble metal salt of a phenol-formaldehyde novolak resin made by procedures described in U.S. Pat. Nos. 3,732,120 and 3,455,721 (CF 1), silton clay (CF 2), or a metal salt of an aromatic carboxylic acid described in U.S. Pat. No. 4,022,936 (CF 3). These CB-CF couplets were then subjected to a calender intensity (CI)test.

A CI test is essentially a rolling pressure test and is conducted to determine the amount of color developed from the transfer of marking liquid obtained by such rolling pressure. The results are reported as the ratio of the reflectance of the marks produced on the CF sheet as compared to the background reflectance of the CF paper ($I/I_o$) expressed as a percentage. In the CI test the lower the value, the more intense the mark.

The CI results listed in Table XIV were obtained from the indicated CB-CF pairs:

TABLE XIV

| CB Sheets | Calender Intensity ($I/I_o$%) | | |
|---|---|---|---|
| | CF 1 | CF 2 | CF 3 |
| Ex. 40 | 56 | 59 | 48 |
| Ex. 41 | 64 | 61 | 69 |
| Ex. 42 | 61 | 56 | 62 |

The invention being thus described, it will be obvious that the same may be varied in many ways. Such variations are not to be regarded as a departure from the spirit and scope of the invention, and all such modifications are intended to be included within the scope of the following claims.

What is claimed is:

1. A compound represented by the formula:

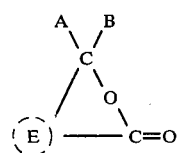

wherein E is:

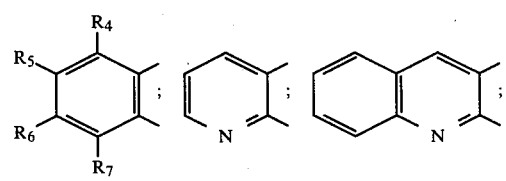

-continued

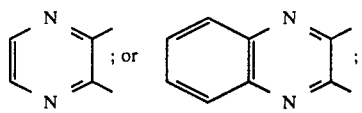

$R_4$, $R_5$, $R_6$ and $R_7$ are: hydrogen, chlorine or dialkylamino;

A is:

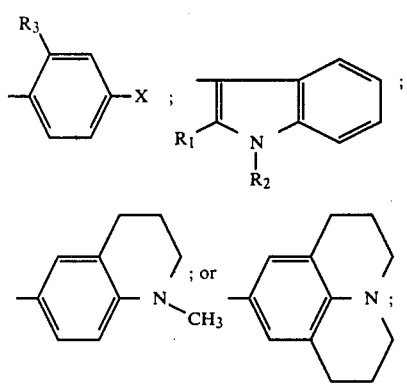

X is:

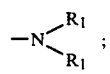

or morpholino;

$R_1$ and $R_2$ are: hydrogen, alkyl, phenyl or methyl phenyl;

$R_3$ is: hydrogen, alkoxy or chlorine;

B is:

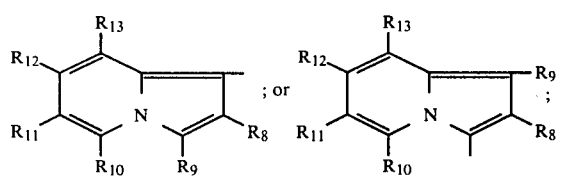

$R_8$ is: phenyl, phenyl which is substituted by methoxy, phenyl, chloro or dimethylamino, naphthyl, pyridyl or alkyl;

$R_9$ is: hydrogen, alkyl or phenyl; and $R_{10}$, $R_{11}$, $R_{12}$ and $R_{13}$ are: hydrogen or alkyl.

2. The compound of claim 1 wherein A is

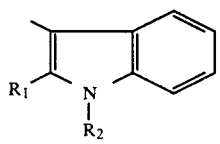

3. The compound of claim 2 wherein E is

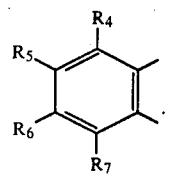

4. The compound of claim 2 wherein E is

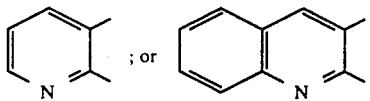

5. The compound of claim 2 wherein E is

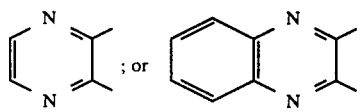

6. The compound of claim 3 wherein $R_8$ is phenyl.

7. The compound of claim 6 wherein $R_1$ and $R_2$ are alkyl.

8. The compound of claim 1 wherein A is

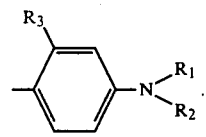

9. The compound of claim 8 wherein E is

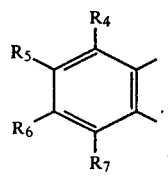

10. The compound of claim 8 wherein E is

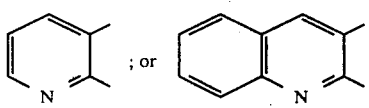

11. The compound of claim 8 wherein E is

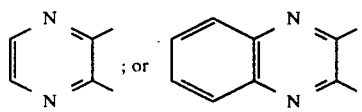

12. The compound of claim 9 wherein $R_6$ is dialkylamino.

13. The compound of claim 12 wherein $R_1$ and $R_2$ are alkyl.

14. The compound of claim 13 wherein $R_8$ is phenyl.

15. The compound of claim 10 wherein $R_1$ and $R_2$ are alkyl.

16. The compound of claim 15 wherein $R_8$ is phenyl.
17. The compound of claim 1 wherein B is

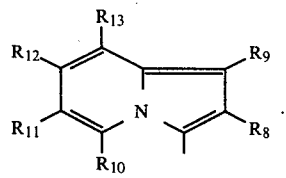

18. The compound of claim 17 wherein E is

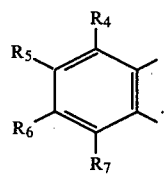

19. The compound of claim 18 wherein A is

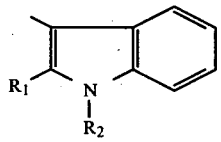

20. The compound of claim 19 wherein $R_4$, $R_5$, $R_6$, $R_7$, $R_{10}$, $R_{11}$, $R_{12}$ and $R_{13}$ are hydrogen.
21. The compound of claim 20 wherein $R_8$ is phenyl, phenyl which is substituted by methoxy, phenyl, chloro or dimethylamino or naphthyl.
22. The compound of claim 21 wherein $R_1$ and $R_2$ are alkyl.
23. The compound of claim 22 wherein:
$R_1$ and $R_9$ are methyl; and
$R_2$ is ethyl.
24. The compound of claim 23 wherein $R_8$ is phenyl.
25. The compound of claim 23 wherein $R_8$ is 2-naphthyl.
26. The compound of claim 22 wherein:
$R_1$ is methyl;
$R_2$ is ethyl; and
$R_9$ is hydrogen.
27. The compound of claim 26 wherein $R_8$ is phenyl.
28. The compound of claim 19 wherein $R_4$, $R_5$, $R_6$, $R_7$, $R_9$, $R_{10}$, $R_{12}$ and $R_{13}$ are hydrogen.
29. The compound of claim 28 wherein $R_8$ is phenyl, phenyl which is substituted by methoxy, phenyl, chloro or dimethylamino or naphthyl.
30. The compound of claim 29 wherein $R_1$, $R_2$ and $R_{11}$ are alkyl.
31. The compound of claim 30 wherein:
$R_2$ and $R_{11}$ are ethyl; and
$R_1$ is methyl.
32. The compound of claim 31 wherein $R_8$ is para-methoxyphenyl.
33. The compound of claim 22 wherein:
$R_1$ is methyl;
$R_2$ is ethyl; and
$R_8$ and $R_9$ are phenyl.
34. The compound of claim 18 wherein A is

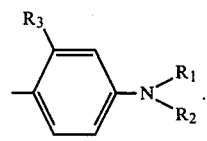

35. The compound of claim 34 wherein $R_3$, $R_4$, $R_5$, $R_7$, $R_{10}$, $R_{11}$, $R_{12}$ and $R_{13}$ are hydrogen.
36. The compound of claim 35 wherein $R_8$ is phenyl, phenyl which is substituted by methoxy, phenyl, chloro or dimethylamino or naphthyl.
37. The compound of claim 36 wherein:
$R_1$, $R_2$ and $R_9$ are alkyl; and
$R_6$ is dialkylamino.
38. The compound of claim 37 wherein:
$R_1$ and $R_2$ are methyl; and
$R_6$ is dimethylamino.
39. The compound of claim 38 wherein:
$R_8$ is phenyl; and
$R_9$ is methyl.
40. The compound of claim 35 wherein $R_8$ is 2-pyridyl.
41. The compound of claim 40 wherein:
$R_1$ and $R_2$ are alkyl;
$R_6$ is dialkylamino; and
$R_9$ is hydrogen or phenyl.
42. The compound of claim 41 wherein:
$R_1$ and $R_2$ are methyl;
$R_6$ is dimethylamino; and
$R_9$ is phenyl.
43. The compound of claim 40 wherein:
$R_1$ and $R_2$ are methyl;
$R_6$ is dimethylamino; and
$R_9$ is hydrogen.
44. The compound of claim 17 wherein E is

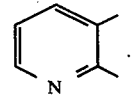

45. The compound of claim 44 wherein A is

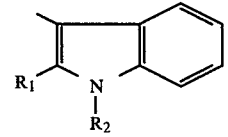

46. The compound of claim 45 wherein $R_{10}$, $R_{11}$, $R_{12}$ and $R_{13}$ are hydrogen.
47. The compound of claim 46 wherein $R_8$ is phenyl, phenyl which is substituted by methoxy, phenyl, chloro or dimethylamino, or naphthyl.
48. The compound of claim 47 wherein:
$R_1$ is methyl;
$R_2$ is ethyl; and
$R_9$ is hydrogen.
49. The compound of claim 48 wherein $R_8$ is phenyl.
50. The compound of claim 47 wherein:
$R_1$ is methyl;
$R_2$ is ethyl; and
$R_8$ and $R_9$ are phenyl.
51. The compound of claim 17 wherein E is

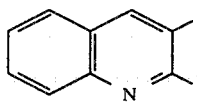

52. The compound of claim 51 wherein A is

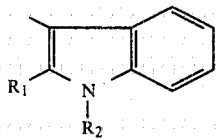

53. The compound of claim 52 wherein $R_{10}$, $R_{11}$, $R_{12}$ and $R_{13}$ are hydrogen.
54. The compound of claim 53 wherein:
$R_1$ and $R_9$ are methyl;
$R_2$ is ethyl; and
$R_8$ is phenyl.
55. The compound of claim 44 wherein A is

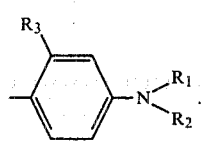

56. The compound of claim 55 wherein $R_{10}$, $R_{11}$, $R_{12}$ and $R_{13}$ are hydrogen.
57. The compound of claim 56 wherein $R_8$ is phenyl, phenyl which is substituted by methoxy, phenyl, chloro or dimethylamino or naphthyl.
58. The compound of claim 57 wherein:
$R_1$ and $R_2$ are ethyl;
$R_3$ is ethoxy; and
$R_9$ is methyl.
59. The compound of claim 58 wherein $R_8$ is phenyl.
60. The compound of claim 57 wherein:
$R_1$ and $R_2$ are ethyl;
$R_3$ is ethoxy;
$R_8$ is phenyl; and
$R_9$ is hydrogen.
61. The compound of claim 1 wherein B is

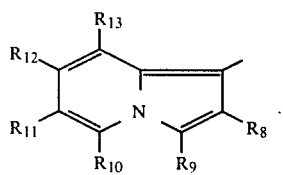

62. The compound of claim 61 wherein E is

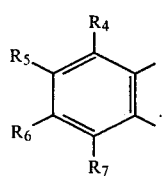

63. The compound of claim 62 wherein A is

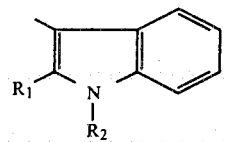

64. The compound of claim 63 wherein:
$R_4$, $R_5$, $R_6$ and $R_7$ are chlorine; and
$R_{10}$, $R_{11}$, $R_{12}$ and $R_{13}$ are hydrogen.
65. The compound of claim 64 wherein $R_1$ and $R_2$ are alkyl.
66. The compound of claim 65 wherein $R_8$ and $R_9$ are alkyl.
67. The compound of claim 66 wherein:
$R_1$, $R_8$ and $R_9$ are methyl; and
$R_2$ is ethyl.
68. The compound of claim 61 wherein E is

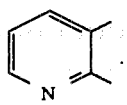

69. The compound of claim 68 wherein A is

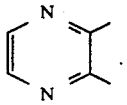

70. The compound of claim 69 wherein:
$R_{10}$, $R_{11}$, $R_{12}$ and $R_{13}$ are hydrogen;
$R_2$ is etyl; and
$R_1$, $R_8$ and $R_9$ are methyl.
71. The compound of claim 61 wherein E is

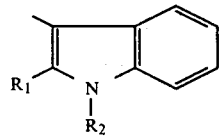

72. The compound of claim 71 wherein A is

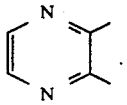

73. The compound of claim 72 wherein $R_{10}$, $R_{12}$ and $R_{13}$ are hydrogen.
74. The compound of claim 73 wherein $R_8$ is phenyl, phenyl which is substituted by methoxy, phenyl, chloro or dimethylamino or naphthyl.
75. The compound of claim 74 wherein:
$R_1$ and $R_9$ are methyl; and
$R_2$ and $R_{11}$ are ethyl.
76. The compound of claim 75 wherein $R_8$ is phenyl.
77. The compound of claim 61 wherein E is

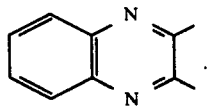

78. The compound of claim 77 wherein A is

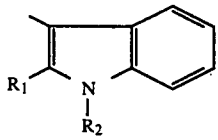

79. The compound of claim 78 wherein:
$R_{10}$, $R_{11}$, $R_{12}$ and $R_{13}$ are hydrogen;
$R_1$ and $R_9$ are methyl;
$R_2$ is ethyl; and
$R_8$ is phenyl.

80. A method of marking on a substrate by developing colored materials from chromogenic compounds according to claim 1 comprising: providing and bringing into contact at least one of said chromogenic compounds, in areas on said substrate where marking is desired, with an electron-accepting Lewis acid material to produce marks in said areas of a colored material formed by the action of said electron-accepting material on said chromogenic compound.

81. A pressure-sensitive record unit comprising:
(a) mark-forming components comprising at least one chromogenic compound according to claim 1 and an electron-accepting Lewis acid material reactive with the chromogenic compound;
(b) support web or sheet material; and
(c) a releasable liquid solvent for the mark-forming components arranged in continguous juxtaposition with the mark-forming components and supported by the sheet material, wherein the mark-forming components upon pressure release of the liquid solvent are brought into reactive contact in the released solvent.

82. The record unit of claim 81 wherein at least one of the mark-forming components is maintained in isolation from the other mark-forming components prior to the release of the solvent.

83. The record unit of claim 81 wherein the liquid solvent is present as the nucleus of a microcapsule.

* * * * *

UNITED STATES PATENT AND TRADEMARK OFFICE
CERTIFICATE OF CORRECTION

PATENT NO. : 4,232,887

DATED : November 11, 1980

INVENTOR(S) : William J. Becker, et al.

It is certified that error appears in the above-identified patent and that said Letters Patent are hereby corrected as shown below:

Column 28, Claim 70, line 39,
    change "etyl" to --ethyl--.

Column 30, Claim 81, line 13,
    change "continguous" to --contiguous--.

Signed and Sealed this

Tenth Day of February 1981

[SEAL]

Attest:

RENE D. TEGTMEYER

Attesting Officer     Acting Commissioner of Patents and Trademarks